US009891206B2

(12) United States Patent
Van Hal et al.

(10) Patent No.: US 9,891,206 B2
(45) Date of Patent: Feb. 13, 2018

(54) BACK TITRATION METHODS FOR SCALING CATIONS AND DOWNHOLE TOOLS FOR PERFORMING SUCH METHODS

(71) Applicant: SCHLUMBERGER TECHNOLOGY CORPORATION, Sugar Land, TX (US)

(72) Inventors: Ronald E. G. Van Hal, Belmont, MA (US); Jane T. Lam, Randolph, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 663 days.

(21) Appl. No.: 14/152,835

(22) Filed: Jan. 10, 2014

(65) Prior Publication Data
US 2015/0198037 A1    Jul. 16, 2015

(51) Int. Cl.
G01P 15/00    (2006.01)
G01N 33/20    (2006.01)

(52) U.S. Cl.
CPC .................................... *G01N 33/20* (2013.01)

(58) Field of Classification Search
CPC ................................ E21B 49/08; G01N 33/20
USPC ....................................................... 73/152.42
See application file for complete search history.

(56) References Cited

U.S. PATENT DOCUMENTS

| | | | | |
|---|---|---|---|---|
| 2,748,790 A | * | 6/1956 | Hodgens, Jr. | ....... A47L 15/0055 137/5 |
| 2,925,431 A | * | 2/1960 | Choppin | ................... C22B 3/24 210/672 |
| 3,663,448 A | * | 5/1972 | Ralston | ..................... C02F 5/14 210/700 |
| 3,732,074 A | * | 5/1973 | Feitler, Jr. | .............. G01N 21/82 210/96.2 |
| 3,738,937 A | * | 6/1973 | Kautsky | ................... C02F 5/14 134/2 |
| 4,190,462 A | | 2/1980 | De Jong et al. | |
| 4,215,000 A | | 7/1980 | De et al. | |
| 4,357,143 A | * | 11/1982 | Scott | ..................... G01N 30/96 204/409 |
| 5,013,453 A | * | 5/1991 | Walker | ..................... C02F 1/52 210/712 |

(Continued)

OTHER PUBLICATIONS

Harold R. R.IcCle4ry, Titration of Bromide and Iodide Ions with Mercuric Nitrate Solution, Jan. 1942, Columbia Cniversity, New York, N. Y., Present address, 29 West High St., Bound Brook. S. J.*

(Continued)

*Primary Examiner* — Eric S McCall
*Assistant Examiner* — Mohammed E Keramet-Amircola

(57) ABSTRACT

A method for determining scaling cation concentration may include introducing a first solution that includes a scaling cation, incrementally adding a portion of the first solution to a volume of a second solution comprising a counter scaling anion and a complexing agent, wherein the second solution comprises a fixed concentration of the counter scaling anion and the agent, to form a mixed solution, adding the first solution to the second solution until a precipitate of the scaling cation and the counter scaling anion forms, and determining the scaling cation concentration of the first solution.

23 Claims, 7 Drawing Sheets

(56) References Cited

U.S. PATENT DOCUMENTS

| | | | | |
|---|---|---|---|---|
| 5,302,531 | A | * | 4/1994 | Bauer .................... G01N 33/52 436/74 |
| 5,494,700 | A | * | 2/1996 | Anderson ............ B01D 53/228 427/115 |
| 8,826,981 | B2 | | 9/2014 | Van Hal et al. |
| 2009/0269261 | A1 | * | 10/2009 | Kim ........................ C01G 43/01 423/16 |
| 2010/0175467 | A1 | * | 7/2010 | DiFoggio .............. E21B 49/087 73/152.28 |
| 2011/0070487 | A1 | * | 3/2011 | Padhi .................... C01G 45/02 429/206 |

OTHER PUBLICATIONS

Anderegg, et al., "Critical evaluation of stability constants of metal complexes of complexones for biomedical and environmental applications", Pure Appl. Chem., vol. 77, No. 8, 2005, pp. 1445-1495.

Arnaud-Neu, et al., "Critical evaluation of stability constants and thermodynamic functions of metal complexes of crown ethers", Pure and Applied Chemistry, vol. 75, Issue 1, 2003, pp. 71-102.

Barouda, et al., "Barium Sulfate Crystallization in the Presence of Variable Chain Length Aminomethylenetetraphosphonates and Cations (Na+ or Zn2+)", Crystal Growth & Design, vol. 7, Issue 2, 2007, pp. 321-327.

Bordunov, et al., "Synthesis and Properties of 5-Chloro-8-hydroxyquinoline-Substituted Azacrown Ethers: A New Family of Highly Metal Ion-Selective Lariat Ethers", Inorg. Chem., vol. 35, Issue 25, 1996, pp. 7229-7240.

Dantz, et al., "Effects of the benzosubstitution of cryptands for the complex formation between protons, alkali and alkaline earth cations in water", Polyhedron, vol. 17, Issues 11-12, May 30, 1998, pp. 1891-1895.

Drumhiller, et al., "Spectrophotometric titration of cryptands and compleximetric titration of barium with cryptand (2.2.2)", Analytica Chimica Acta, vol. 162, Aug. 1, 1984, pp. 315-321.

Popov, et al., "Critical Evaluation of Stability Constants of Phosphonic Acids", Pure Appl. Chem., vol. 73, No. 10, 2011, pp. 1641-1677.

* cited by examiner

BACK TITRATION METHODS FOR SCALING CATIONS AND DOWNHOLE TOOLS FOR PERFORMING SUCH METHODS

BACKGROUND

Scale deposition is one of the most serious concerns for the petroleum industry. Scale deposition is the leading cause of declining petroleum production worldwide. Scale removal, scale control and deferred petroleum production costs the petroleum industry millions of dollars each year. Scale is an assembly of hard inorganic crystals that cake perforations, casing production tubing, valves, pumps and downhole completion equipment, thereby clogging the wellbore and preventing fluid flow.

Alkali metal cations such as barium ($Ba^{2+}$), calcium ($Ca^{2+}$), and strontium ($Sr^{2+}$) present in the formation fluids are responsible for scale formation. When these alkali metal cations come into contact with sulfate and/or carbonate anions from the drilling and or stimulation fluid, they precipitate and create scale. Of the three scaling cations precipitated by sulfate, barium sulfate has the lowest solubility ($BaSO_4=1\times10^{-10}$ M, $CaSO_4=5\times10^{-5}$ M, and $SrSO_4=3\times10^{-7}$ M) and is therefore a primary target for the prediction of scale formation, which can be delayed or prevented by using an inhibitor.

Conventional methods for determining scaling cation concentration, in addition to not being well suited for downhole applications, have detrimental flaws which necessitate improvements.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method for determining scaling cation concentration, which may include introducing a first solution that includes a scaling cation, incrementally adding a portion of the first solution to a volume of a second solution comprising a counter scaling anion and a complexing agent, wherein the second solution comprises a fixed concentration of the counter scaling anion and the agent, to form a mixed solution, adding the first solution to the second solution until a precipitate of the scaling cation and the counter scaling anion forms, and determining the scaling cation concentration of the first solution.

In another aspect, embodiments disclosed herein relate to a method for determining scaling cation concentration of a fluid sample within a wellbore, which may include extracting a fluid sample comprising scaling cations from a wellbore and/or formation; iteratively adding portions of the extracted fluid sample to a volume of a first solution comprising a counter scaling anion and a complexing agent, wherein the second solution comprises a fixed concentration of the counter scaling anion and the complexing agent, to form a mixed solution; and optically interrogating the mixed solution to detect precipitation of a scaling cation-counter scaling anion compound.

In yet another aspect, embodiments disclosed herein relate to a method for determining the scaling cation concentration of a fluid sample within a wellbore, which may include injecting a solution comprising a counter scaling anion, a complexing agent, and a scaling cation insensitive dye into a wellbore flowline containing a wellbore or formation fluid comprising a scaling cation to create a mixed solution; determining if precipitation of a scaling cation-counter scaling anion compound has occurred in the mixed solution; determining the concentration of the complexing agent in the mixed solution by calculating the mixing ratio of the solution injected and the wellbore or formation fluid based on the optical density of the scaling cation insensitive dye in the mixed solution; and determining the scaling cation concentration by extrapolating to the endpoint the plot of absorbance versus the volume of wellbore fluid in the mixed solution of at least two measurements correlated to mixed solutions with different mixing ratios that show precipitation of a scaling cation-counter scaling anion compound.

Other aspects and advantages of the claimed subject matter will be apparent from the following description and the appended claims.

DETAILED DESCRIPTION

In one aspect, embodiments disclosed herein relate to a titration method for determining scaling cation concentration. More particularly, embodiments disclosed herein relate to the titration of a mixture of counter scaling anions and at least one complexing agent with a solution containing an unknown concentration of scaling cations.

In the laboratory, there are two main routes for the determination of the barium concentration: reaction with sulfate to measure the light scattering of the crystals produced or colorimetric detection by the use of a color agent. An unknown barium concentration in a formation fluid sample can be determined by the addition of sulfate anions, whereby, upon addition of sulfate, barium sulfate will form and precipitate, causing a turbid solution that looks white due to the scattering of light by the precipitated crystals. The turbidity and light scattering ability of the solution containing precipitated barium sulfate depends on the concentration, size and shape of the crystals of barium sulfate. As barium sulfate is not absorbent, the reduction in light intensity during an absorption measurement is due to the light scattering of the crystals. It has been shown that this method gives a linear relation between the barium concentration and optical absorption due to scattering, implying that the shape and size of the crystals do not vary drastically when the barium concentration is increased. The uncertainty in the measurement was found to be roughly 18%; however, the presence of other scaling cations in the solution can contribute to the error in the measurement.

Figure 1:
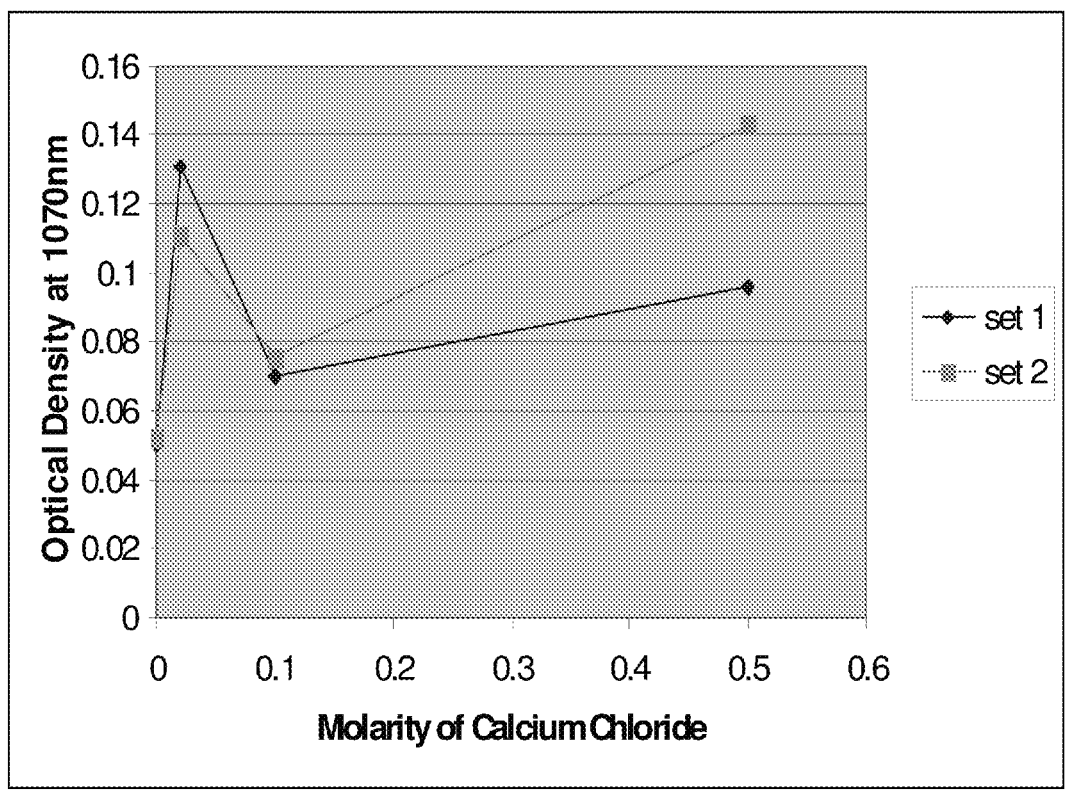
FIG. 1 is a plot showing the optical density results of a 2.1 mM $Ba^{2+}$ solution with different concentrations of calcium, to which is added sulfate to form a 20 mM sulfate solution.

FIG. 1 shows optical density results of a 2.1 mM $Ba^{2+}$ solution to which is added various concentrations of $Ca^{2+}$, another scaling cation. After the added $Ca^{2+}$ is allowed to dissolve completely, sulfate is added to form a 20 mM sulfate solution. As can be seen in FIG. 1, the resulting optical density is not a simple function of the $Ca^{2+}$ concentration and it has so far been impossible to interpret the results.

Colorimetric detection of barium can be done with the use of an ionochromic dye that undergoes either a color change or increases the current color intensity in the presence of barium. Rhodizonate is an example of a dye that shows a color change equivalent to a peak wavelength shift of about 40 nm. However, the dye solution has to be prepared and used immediately because the absorbance at the representative wavelength disappears completely in 30 minutes at pH 7. Additionally, cresolphthalein, methylthymol blue, eriochrome black T, and others intensify in the presence of barium, but must also be prepared and used quickly as they show a strong decrease in absorbance after one hour at 80° C. The use of such conventional/laboratory bench top techniques for determining scaling cation concentration on samples obtained from downhole is often not sufficient because many drilling fluids contain sulfates, which can cause scaling cation precipitation during the sample acquisition and storage prior to testing. This precipitation may lead to an underestimation of the concentration of scaling cations when the sample is tested. However, an estimation of the concentration of the scaling cations present in the formation fluids would help to optimize the amount of scale inhibitor added to various fluids during production or other downhole operations.

Titration is a laboratory method for quantitative chemical analysis, and is used to determine the unknown concentration of a known analyte. In a titration, a reagent, called the titrant, of a known concentration is used to react with a solution of the analyte. By monitoring the volume of titrant added, it is possible to determine the exact amount that has been consumed when the endpoint, the point at which all the analyte has been consumed, is reached. Generally, the endpoint is determined by a sudden color change, precipitation, or other property change. In cases where it is hard to determine the exact endpoint, a back titration may be used. In a back titration, an excess of reagent is added and subsequently a titration is performed to determine the excess of the reagent.

In one or more embodiments of the present disclosure, a solution containing scaling cations (such as $Ba^{2+}$, $Ca^{2+}$, and $Sr^{2+}$) in an unknown concentration may be incrementally added to a known volume of a solution containing a counter scaling anion (such as the sulfate anion) and at least one complexing agent, both of known concentrations, to form a mixed solution. The solution of unknown concentration may be incrementally added to the solution of known concentrations to form a mixed solution until a scaling cation-counter scaling anion precipitate forms in the mixed solution.

In one or more embodiments, the counter scaling anions are chosen from among those anions resulting in a barium salt with a solubility product less than $1\times10^{-6}$. In more particular embodiments, sulfate ($SO_4^{-2}$), sulfite ($SO_3^{-2}$), thiosulfate ($S_2O_3^{-2}$), iodate ($IO_3^{-}$), fluoride ($F^{-}$), and mixtures of anions thereof may be utilized.

Figure 2:
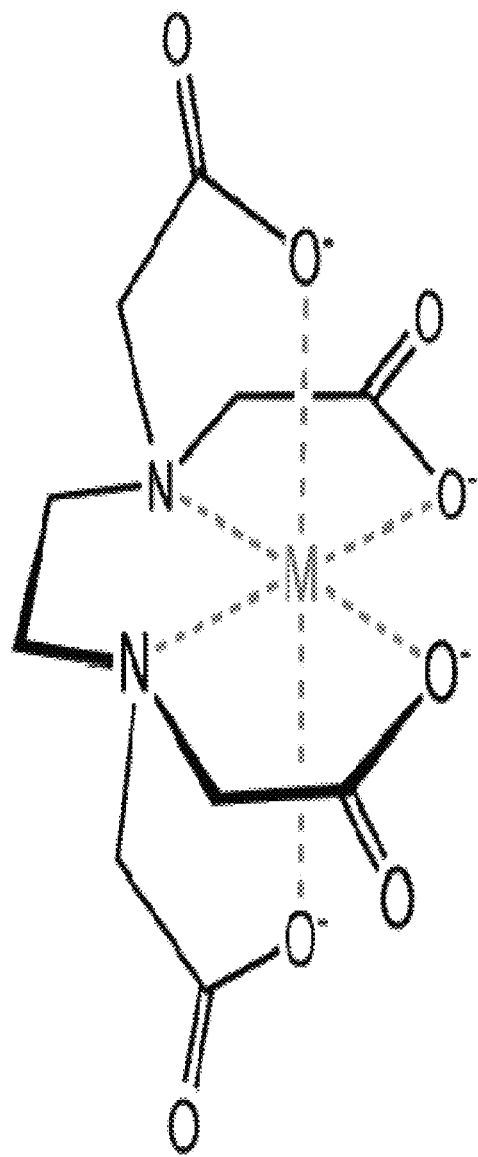
FIG. 2 is a schematic representation of the complexation of a metal ion (M) with EDTA.

In one or more embodiments, the complexing agent is chosen to have a stronger stability constant with the scaling cations than the stability constant of the counter scaling anions with the scaling cations. A stability constant (formation constant, binding constant) is an equilibrium constant for the formation of a complex in solution. Thus, it is a measure of the strength of the interaction between the scaling cation and the complexing agent, which come together to form a scaling cation-complexing agent complex. In this way, the complexing agents prevent precipitation of a scaling cation-counter scaling anion precipitate until all (or substantially all) of the complexing agent has been complexed with a scaling cation, after which the excess scaling cations complex with the available counter scaling anions to form a scaling cation-counter scaling anion precipitate. For example, one embodiment may use an unknown concentration of $Ba^{2+}$ as the scaling cation, sulfate anion ($SO_4^{-2}$) as the counter scaling anion, and ethylenediaminetetraacetic acid (EDTA) as the complexing agent. FIG. 2 shows a schematic representation of the complexation of EDTA with a metal ion (M), which may be the scaling cation. Once a precipitate is formed, the scaling cation concentration may be determined by relating the volumetric amount of the solution containing scaling cations that is added to the known volume of the solution with a known concentration of the at least one complexing agent by applying the following equation:

$$X = [Y] * \frac{V_1}{V_2}$$

wherein X is the unknown scaling cation concentration, [Y] is the total complexing agent concentration, $V_1$ is the volume of the solution containing complexing agent and counter scaling anion, $V_2$ is the volume of the solution containing scaling cations that is added.

If the initial concentration of counter scaling anion is over about 10 times the concentration of the at least one complexing agent, some precipitation may start to occur prematurely due to competitive reactions between the counter scaling anion and the complexing agent for the $Ba^{2+}$ and other scaling cations present. In this case, the concentration of scaling cations in the mixed solution may be overestimated by the above method, and therefore, in one or more embodiments, the concentration of counter scaling anion in the solution containing complexing agent and counter scaling anion may be up to 10 times the concentration of the at least one complexing agent. In a particular embodiment, counter scaling anion may be present in the solution at a concentration of up to about 10 mM or at least about 1 mM in other embodiments. The concentration of the complexing agent may be present in the range of 0.1 to 1 times the concentration of the counter scaling anion. As the concentration of the counter scaling anion is increased, lower concentrations of scaling cations will be precipitated. Thus, depending on the type of and solubility of the precipitated scaling cation-counter scaling anion, the concentration of counter scaling anion may be varied accordingly.

In one or more embodiments, the scaling cations may include cations of at least one of $Ba^{2+}$, $Ca^{2+}$, or $Sr^{2+}$, and in particular embodiments a mixture of two or more scaling cations including but not limited to $Ba^{2+}$, $Ca^{2+}$, or $Sr^{2+}$. By utilizing a solution containing a mixture of counter scaling anions and at least one complexing agent over a solution containing a mixture of counter scaling anions alone, the concentration of the scaling cations that is determined is based upon the onset point of precipitation and not by the scattering intensity, which presents a non-linear relation in the presence of multiple scaling cations. Advantageously, in the presence of multiple scaling cations, the currently described method gives a total scaling cation concentration, as the complexing agent may complex with each type of scaling cations in the sample fluid.

In one or more embodiments, the complexing agent may be selected to have a stronger stability constant ($pK \geq 8$) with the cations of $Ba^{2+}$, $Ca^{2+}$, or $Sr^{2+}$ relative to non-scale cations ($pK \leq 5$). Depending on the actual stability constant value with the scaling cations, the actual stability constant with non-scale cations may be less ($\Delta pK \geq 3$) than that of the scaling cations. There are many types of complexing agents that may be utilized, with inhibitors that are used to control scale and/or complexing agents used in potentiometric sensors typically capable of performing the presently desired function. Description of such types of complexing agents follows.

Complexones are a series of artificial amino acids, containing normally at least one iminodiacetic acid group, $N(HCH_2COOH)_2$, or two aminoacetic acid groups, $NHCH_2COOH$. They typically possess high stability constant values due to the cumulative affect of their basic amino groups and the high negative charge provided by the carboxylate groups, as well as their formation of numerous stable five-membered chelate rings with a metal cation. In one or more embodiments, the complexone binds stronger to $Ba^{2+}$, $Ca^{2+}$ and $Sr^{2+}$ than to other metal cations. Ethylenediaminetetraacetic acid (EDTA) is a strong chelating agent ($pK=9.62$) that is useful in cases where the formation water contains negligible amounts of other polyvalent cations. Cations like $Fe^{2+}$, $Fe^{3+}$ and $Cu^{2+}$ have a stronger stability constant than barium and will thus interfere with the measurement. Common cations like sodium ($Na^+$) and potassium ($K^+$) have a much weaker stability constant and will not interfere with the proposed measurement. Calcium and strontium have a stronger stability constant than barium and thus a total scaling cation concentration, or hardness, can be measured. EDTA is one of a series of complexones that can be used as a chelating agent and is known to have one of the strongest stability constants. Other examples include nitriloacetic acid (NTA) and diethylene triamine pentacetic acid (DTPA) but they show similar interference in the presence of other polyvalent cations and in general show poor results at elevated temperatures. DOTA (2,2,2,2-(1,4,7,10-tetraazacyclododecane) tetraacetic acid) is another example with a strong stability constant ($pK=12.9$). The stability constant of $Ba^{2+}$ with DOTA is a factor 4 higher than that with DTPA ($pK=8.8$) and is also higher than the stability constant of magnesium ($Mg^{2+}$) with DOTA. This makes DOTA a particularly useful complexing agent since the most commonly interfering cations will not interfere with the measurements. However, several less common cations like cadmium, cobalt and others will interfere. Selection for such complexones may be based, for example, on the cations expected to be present in the fluid being investigated.

In one or more embodiments, the complexing agent may comprise at least one iminodiacetic acid group, $N(HCH_2COOH)_2$, or two aminoacetic acid groups, $NHCH_2COOH$, as with EDTA, NTA, DTPA, and DOTA.

Phosphonates are the phosphonic acid containing analogues of complexones. They may be used to prevent the precipitation of calcium salts in laundry detergents and as corrosion inhibitors. Phosphonates have their greatest affinity for metal cations when present as fully dissociated species. Additionally, they are often able to prevent precipitation of scaling cations at sub-stochiometric levels. It has been found that in its single protonated form EDTMP (ethylenediaminetetra(methylynephosphonate)), the phosphonate equivalent of EDTA has a strong affinity for $Ba^{2+}$ ($pK=10.26$). Thus, the solution has to be around pH 13 for EDTMP to be effective. Also, EDTMP has a higher stability constant with $Ba^{2+}$ than with zinc ($Zn^{2+}$) although other stability constants are not accurately known.

In yet another embodiment, the complexing agent may comprise phosphonic acid groups, as with ethylenediaminetetra(methylenephosphonic acid) (EDTMP), tetramethylenediaminetetra(methylenephosphonic acid) (TDTMP), hexamethylenediaminetetra(methylenephosphonic acid) (HDTMP), nitrilo tri(methyl phosphonic acid) (NTMP), diethylenetriaminepenta(methylenephosphonic acid) (DTPMP).

Crown ethers are compounds with multiple (3 or more) oxygen atoms incorporated in a mono cyclic carbon backbone. The nature of their binding sites and the presence of a hydrophobic cavity delineated by a lipophilic envelope causes crown ethers to exhibit a strong affinity and high selectivity for alkali and alkaline earth metal cations. The main factor governing the stability constant and selectivity is the size adequacy between the cation and the cavity created by the crown ether ligand. The cations fitting the cavity best are located in its center thereby optimizing the interactions with the oxygen atoms. The ionic radii and the cavity radii of many cations and crown ethers are known and the highest selectivity are expected when their radius ratios are closest to one. The ionic radius of barium is 136 pm whereas the cavity radius of 18-crown-6 is 130 pm. However, the stability constant is a pK of about 3.79, which is much lower than the stability constants of the complexones. In some embodiments, methanol may be utilized as a solvent and will increase the stability constant to 7.2. Methanol/water mixtures will give stability constants in between the water and the methanol stability constant. The use of 18-crown-6 has the advantage over the complexones in that it binds stronger to $Ba^{2+}$ than most other cations with lead ($Pb^{2+}$) being the exception. It has also been shown that a number of benzo-21-crown-7 and dibenzo-21-crown-7 compounds have a strong affinity for $Ba^{2+}$, which is in most cases stronger than that for strontium and much stronger ($\Delta pK>3$) than calcium and magnesium. Further, 3,5-di-t-butyl-benzo-21-crown-7 has a much stronger affinity for barium than for any of the other alkaline earth metal cations; thus, showing that crown ethers may be substituted to modify and improve the stability constant and selectivity towards $Ba^{2+}$. In some embodiments, one or more of the oxygen atoms in crown ethers can be replaced by other hetero atoms like nitrogen to modify their stability constant and selectivity towards $Ba^{2+}$. It has been shown that diaza-crown ethers can remove barium sulfate scaling and they thus may be a candidate for the complexing agent in this measurement. Diaza-crown ethers can be further modified to make them more specific for barium. It has been shown that the sensitivity for barium can be increased dramatically by their substitution with 5-chloro-8-hydroxyquinoline. A stability constant with $Ba^{2+}$ of pK 12.2 can be achieved which is a factor 6 higher than the sensitivity towards any other tested metal.

Cryptands are macrobicyclic polyoxa-diamines that are known for their ability to form stable complexes with alkali, alkaline earth and heavy metal cations. They can be seen as diaza-crown ethers with an extra bridge between the two nitrogen atoms. It has been shown that certain cryptands have excellent stability with barium and are able to dissolve barium sulfate. The simple cryptand(2,2,2) has a strong stability constant with $Ba^{2+}$ (pK=9.5) which is stronger than strontium ($Sr^{2+}$) and much stronger than any other alkali or alkaline earth metal. The substitution with other groups will alter the stability constant and selectivity but improved results have not been obtained with benzyl substituted cryptands. Cryptand(2,2,2) can be used instead of EDTA in a titration of barium with metalphtalein as an indicator; however, the indicator color change at the endpoint is not particularly sharp and it is important to carefully control the pH and indicator concentration.

In yet another embodiment, the complexing agent comprises at least one crown ether, azacrown ether, cryptand, or substituted analogs thereof. In still yet another embodiment, a mixture of at least two complexing agents may be used.

Downhole Implementation

Figure 3:
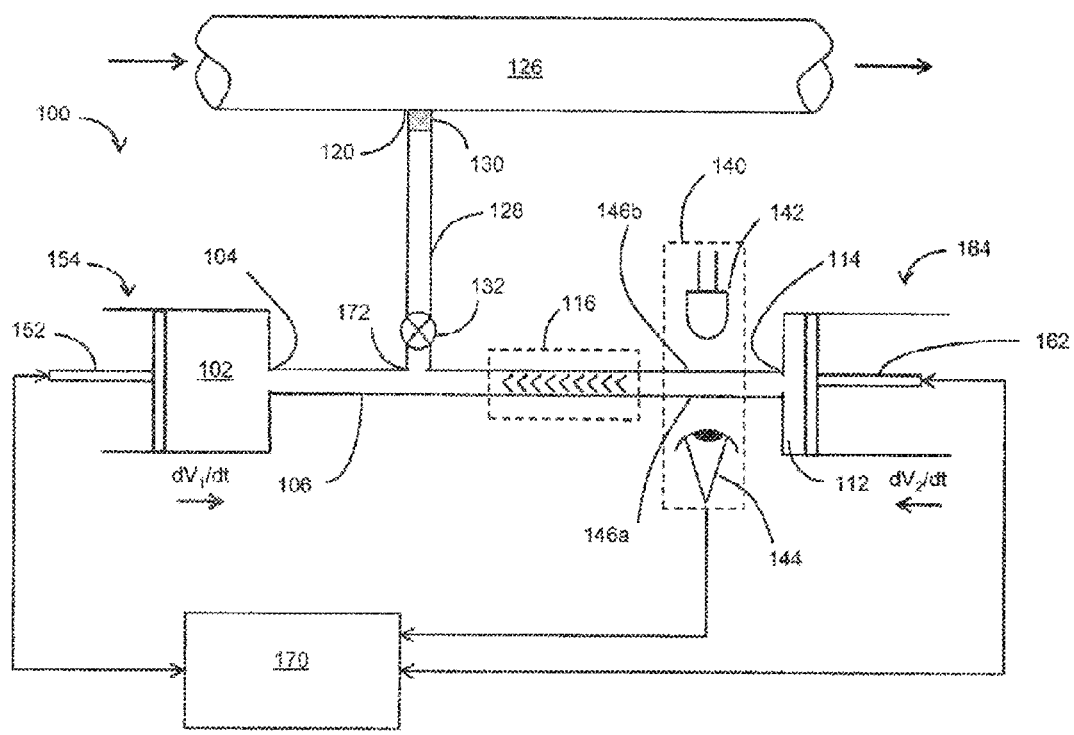
FIG. 3 shows a block diagram of an embodiment of a system for mixing a fluid sample containing scaling cations with a solution containing counter scaling anions and at least one complexing agent under downhole conditions.

In one or more embodiments, a variable volume reservoir (e.g. plunger) based system may be employed to perform the general method disclosed above and determine the concentration of scaling cations in a downhole solution without having to first transport the fluids to the surface. By way of an example, an embodiment of a system 100 for mixing a fluid sample containing scaling cations with a solution containing counter scaling anions and at least one complexing agent is shown in FIG. 3. The system 100 includes a first fluid reservoir 102 having an open end 104 in fluid communication with a fluid conduit 106. A second fluid reservoir 112 is also provided having an open end 114 in fluid communication with the fluid conduit 106. A fluid mixer 116 is serially disposed along the fluid conduit 106 at a location between open ends 104, 114 of the first and second fluid reservoirs 102, 112. The system 100 also includes sample port 120 configured to receive a sample of fluids from a high-pressure flowline 126. In at least some embodiments, flowing within the high-pressure flowline 126 are formation fluids withdrawn from a subterranean formation, such as a hydrocarbon reserve, injected fluids, or mixtures thereof. As such, the sampled fluids may contain combinations of one or more of liquids, gases and suspended solids.

The sample port 120 is also in fluid communication with the fluid conduit 106 at a location between the open end 104 of the first reservoir 102 and the fluid mixer 116. A sampling fluid conduit 128 is configured to be as short as possible to reduce flow resistance and dead volume. One or more filters 130 can be provided to filter fluid flowing from the flowline 126, through the sample port 120 and toward the fluid conduit 106. Such a filter 130 can be used to filter out particles from the fluid sample that might otherwise clog the system or cause an off-set in the measurement.

In at least some embodiments, a valve 132 is provided between the sample port 120 and the fluid conduit 106. For example, an isolation valve 132 is located along the sampling fluid conduit 128. The isolation valve 132 is configured to selectively allow or otherwise block a flow of fluids between the sample port 120 and the fluid conduit 106. So positioned, the isolation valve 132 does not interfere with a flow of fluids between the first fluid reservoir 102, the second fluid reservoir 112, and the fluid mixer 116. The valve 132 is optional but can be included, for example, to prevent leakage of the titrants (e.g., stored in one or more of the first and second reservoirs 102, 112) during transportation and while placing the system 100 into a wellbore. The closed valve 132 can also be used to prevent exposure of the rest of the system 100 to sudden pressure drops and pressure spikes as may be encountered within the flowline 126 during periods of operation.

The system 100 can be configured with a fluid interrogator 140 configured to determine a physical property of a fluid. In the illustrative embodiment, the fluid interrogator 140 is positioned to interrogate a fluid at a location between the fluid mixer 116 and the second fluid reservoir 112. One such fluid interrogator 140 is configured to determine an optical property of a fluid, such as its optical density, also referred to as absorbance. Absorbance is a ratio of a radiant flux absorbed by a body (i.e., fluid) to that incident upon it. Absorption spectroscopy refers to spectroscopic techniques that measure the absorption of radiation, as a function of frequency or wavelength, due to its interaction with a sample. For example, absorption spectroscopy can be employed as an analytical chemistry tool to determine the presence of a particular substance in a sample and, in many cases, to quantify the amount of the substance present.

The example fluid interrogator 140 includes a light source 142 and a light detector 144 (a wavelength dependent detector for spectroscopic applications). At least a portion of the fluid to be interrogated is passed between the light source 142 and the light detector 144. At least a portion of the illumination provided by the light source 142 is directed towards the detector 144, passing through the fluid. In at least some embodiments, windows 146a, 146b are suitably positioned along the fluid conduit 106 to allow such optical interrogation of fluid flowing therewithin. A large scale example of such a tool configured for use downhole within a wellbore include the Live Fluids Analyzer (LFA) or Compositional Fluid Analyzer (CFA) modules of the Modular Formation Dynamics Tester (MDT), a tool suite available in the commercial services provided by Schlumberger, Sugar Land, Tex.

In operation, the first fluid reservoir 102, for example, may be pre-charged with a solution comprising counter scaling anions and at least one complexing agent. A mixture of this pre-charged solution with a fluid sample containing scaling cations obtained from the flowline 126 may produce a detectable change (i.e., precipitation of a scaling cation-counter scaling anion) that can be detected by the one or more fluid interrogators 140.

In the illustrative embodiment, each of the first and second fluid reservoirs 102, 112 are variable-volume reservoirs. For example, each of the fluid reservoirs 102, 112 can include a respective repositionable plunger 152, 162. A repositioning of a plunger 152, 162 within either of the reservoirs 102, 112 changes a volume $V_1$, $V_2$ of the respective reservoir 102, 112 in a corresponding manner. Thus, the two plungers 152, 162 of the illustrative embodiment can be used to manipulate one or more fluids flowing within the fluid conduit 106. A first pump 154, for example, can be used to reposition the first plunger 152, e.g., advancing it toward the open end 104 to effectively push titrant from the reservoir 102 into the fluid conduit 106. Likewise, a second pump 164 can be used to reposition the second plunger 162 away from the open end 114 to effectively draw fluid from the fluid conduit 106 into the second reservoir 112. In a like manner, various combinations of repositioning the first and second plungers 152, 162 can be used to regulate a ratio of titrant and formation/injected fluids within the fluid conduit 106 and particularly within a region of the fluid conduit 106 exposed to the fluid interrogator 140.

The second plunger 162 can be used to pull one or more of sample fluids from the flowline 126 and a titrant from the first reservoir 102 through the fluid conduit 106. The first plunger 152 of the first reservoir 102 containing the titrant can be advanced to push the titrant out of its reservoir 102 through the fluid conduit 106. In situations in which only the second plunger 162 is moving, sample fluids can selectively be drawn from the flowline 126 through sample port 120, presuming the valve 132 is open, and into the fluid conduit 106. Alternatively, by pushing titrant from the first reservoir 102 using the first plunger 152, while simultaneously drawing fluid into the second reservoir 112 using the second plunger 162 to achieve an equivalent change in volume between the two reservoirs 102, 112, a controlled flow of fluids can be achieved that selectively pulls titrant into the fluid channel, without drawing sample fluid into the fluid conduit 106. This result can be achieved even though a valve 132, if present, is open.

More particularly, when the first and second plungers 152 and 162 are moved to provide an equivalent rate of change of volumes of each respective reservoir 102, 112, but in an opposite sense (i.e., $(dV_1/dt)=(-dV_2/dt)$), fluid from the sampling fluid conduit 128 is prevented from entering the fluid conduit, despite the valve 132 being open. Thus, it is possible to pull only titrant through the fluid conduit 106, despite the fluid conduit 106 being exposed to a pressurized flow of fluids from the flowline 126. A slightly lower rate of change of the first reservoir's volume attained by repositioning of the first plunger 152 (i.e., the titrant plunger) than for the second plunger 162 (i.e., $|dV_1/dt|<|-dV_2/dt|$) results in a controlled flow of reservoir fluids from the sampling fluid conduit 128 and into the fluid conduit 106. By controlling the relative rates of change of volumes of the two reservoirs 102, 112 in such a manner, a known mixing ratio can be obtained within the fluid conduit 106. This mixing ratio can be varied by varying the rate of change of volume of the first reservoir 102, for example, to extend the operating range of the sensor.

In at least some embodiments, a controller 170 is provided to control at least operation of the first and second pumps 154, 164. Pumps, such as syringe pumps, can be calibrated, such that a position of its plunger (x) can be used to determine a volume (V) of an associated reservoir. Likewise, a rate of change plunger position (dx/dt) can be used to determine a rate of change of reservoir volume (dV/dt). Such a processor 170 can be in electrical communication with one or more of the pumps 154, 164 to cause changes in volume of the respective reservoirs 102, 112. Alternatively or in addition, the controller 170 can be in electrical communication with the fluid interrogator 140, to receive status as to any interrogated physical properties of the fluid. Such a processor can include one or more microprocessors, for example, executing a set of pre-programmed instructions. Such preprogrammed instructions can be prepared to conduct one or more analytical protocols. It is conceivable that in at least some embodiments, the controller 170 can be used to control operation of the valve 132. In at least some embodiments, the controller 170 includes a timing reference usable to control one or more if timing, as duration and sequence, and rates fluid transfers.

In at least some embodiments, the system 100 (e.g., the controller 170) includes a user interface and/or a data recorder configured to record or otherwise document analytical results. One or more of the controller, user interface and data recorder can be located downhole, at a surface location, for example, being coupled to various elements of the system 100 through telemetry, or in a distributed configuration with some elements located downhole and others at one or more surface locations. It is also envisioned that some of the surface components can be located in the immediate vicinity of the wellbore, while other surface components can located remotely. Communication between any such remote surface components can be accomplished with any suitable means, such as telecommunications and through the Internet.

Any of the various fluid analysis systems, such as the system 100 illustrated in FIG. 3, are capable of being operated in various operational modes. For example, a first operation mode is referred to herein as continuous mixing. Continuous in relation to the continuous mixing mode suggests that formation/injected fluid sampled from the high-pressure flowline 126 and the titrant are flowing within the system 100 for a sufficient duration to allow the system 100 to reach a state of equilibrium during which a stable signal can be obtained from the fluid interrogator 140. For example, depending upon such features as flow rates, volumes and dead space, the time required to reach equilibrium may take up to a several minutes or more.

In a microfluidic titration, a mixing ratio is varied to determine an endpoint. The mixing ratio can be varied in a stepwise change, continuously, or some combination of stepwise and continuous. A stepwise variation of the mixing ratio is comparable to conducting several measurements for which the mixing ratio is different at every measurement. It is under stood that measurement of any particular mixing ratio can be repeated and, for example, averaged as an indicator of the associated mixing ratio. Just as in a regular titration, the endpoint can be determined by the achievement of an endpoint indicator, such as a color change, precipitation or other detectable property (e.g., changes in pH, salinity).

The volumetric step size used in such an approach should be relatively small, as the endpoint is typically observed by a sudden and dramatic change in the observed physical property, generally occurring between two adjacent steps. In at least some embodiments, the mixture associated with the endpoint is considered as an approximation of the mixture ratio at which the endpoint indicator is observed. In at least some other embodiments, the mixture associated with the endpoint is interpolated between one or more observations before and after the endpoint indicator is observed. Alternatively or in addition, relatively course step size can be used to initially isolate the endpoint as occurring between two adjacent steps. The process then can be repeated between the identified steps at a second, finer step size to more precisely locate a mixture associated with the endpoint. The process can be repeated as necessary for even finer step sizes.

Another operating mode of the various fluid analysis systems described herein is referred to as "flow injection analysis." In flow injection analysis, a small sample of a solution (e.g., sampled formation fluid) is "injected" into a flowing reagent. In some embodiments, the reagent can be injected into a flowing sample. Referring to the system 100 illustrated in FIG. 3, such injection flows can be achieved by having the first plunger 152 advancing at a first rate ($dx_1/dt$) to reduce the volume of the first reservoir 102 according to a first volumetric rate of change ($dV_1/dt$). The second plunger 162 can be withdrawn at a respective rate ($dx_2/dt$), to increase the volume of the second reservoir 112 according to a respective volumetric rate of change ($dV_2/dt$). With valve 132 open, the relative volumetric rates of change can be used to selectively and independently control the relative flows of reagent (from the first reservoir 102) and sampled formation fluid (from the flowline 126) as described above.

For example, the plungers 152, 162 can be advanced/withdrawn to achieve equivalent volumetric rates of change ($-dV1/dt = dV2/dt$). Assuming that formation fluid flowing in the flowline 126 is exposed to the fluid conduit 106 through the sampling fluid conduit 128 (i.e., valve 132 open), a balance in pressures at the junction 172 will result in a substantially pure flow of reagent past the fluid interrogator 140. Sampled formation fluid from the flowline 126 can be introduced and combined with the reagent by changing the relative volumetric rates of change. For example, by selectively withdrawing the second plunger 162 for a short moment at a faster rate (increasing $dx_2/dt$), volumetric rate of change ($dV_2/dt$) of the second reservoir 112 is increased. The difference in change of volumes between the first and second reservoirs 102, 112 (e.g., the second reservoir expanding faster than the first reservoir is collapsing) is taken up by a flow of sampled formation fluids from the sampling fluid conduit 128. The result is a mixture of reagent and fluid sample drawn past the fluid interrogator 140.

The resulting variation in mixture, e.g., from pure reagent to a mixture of reagent and sampled formation fluid, results in a corresponding variation in the detected physical property of the fluid. Using an optical fluid interrogator (e.g., spectrometer), a variation in absorbance of the reagent/mixture can be observed. When tracking an absorbance peak (a corresponding wavelength) indicative of a selective analyte in the sampled formation fluid, a short peak in absorbance versus time (sample number) is detected by the detector 144. The change in absorbance resulting in such a peak corresponds to the mixture of sampled fluid and reagent passing an interrogation zone of the optical fluid interrogator 140. There would likely some a delay between variation of pump rates and detection of absorbance changes resulting from a fluid transit time between the junction 172 at which fluid is introduced to the reagent and the interrogation zone. The peak variation can be analyzed, for example, according to a peak height (i.e., maximum absorbance) or by integrating the area under the absorbance peak.

At least one advantage of flow injection analysis is that a continuous baseline measurement is naturally provided by the flow of substantially pure reagent occurring at times (samples) in between periods in which a mixture of reagent and analyte is detected. Such a baseline can be used to detect variations in one or more of the system 100 and the reagent, and in at least some instances, used to calibrate measurements to account for any offsets observed in the baseline. Furthermore, flow injection analysis is relatively fast and uses a limited amount of fluid sample, such as the relatively small amounts injected during periods of mixing. Flow injection analysis alleviates the need to use sufficient sample and reagent to reach an endpoint or equilibrium as may be done in a continuous mixing mode. Instead, small sample volumes can be used, provided they result in detectable variations of the interrogated property (e.g., absorbance). The ability to analyze sampled formation fluids by using only small volumes is particularly useful for situations in which the occurrence of precipitation is possible, as with the reaction of counter scaling anions with metal cations.

A greater precision, for example, in identifying the presence and/or concentration of scaling cations in solution is expected when a volumetric mixing ratio of the fluid sample (analyte solution) and the titrant (counter scaling anion and complexing agent solution) is known with a high degree of specificity. Such results can be achieved, for example by using very accurate volume changes, as may be obtained by very accurate plunger movement. Another method capable of determining the volumetric mixing ratio of the fluid sample and the titrant to a high degree of specificity may include determining the concentration dependent optical density of a scaling cation insensitive dye upon its addition to the mixed solution. A good example of such a dye is commercially available food color.

Figure 5:
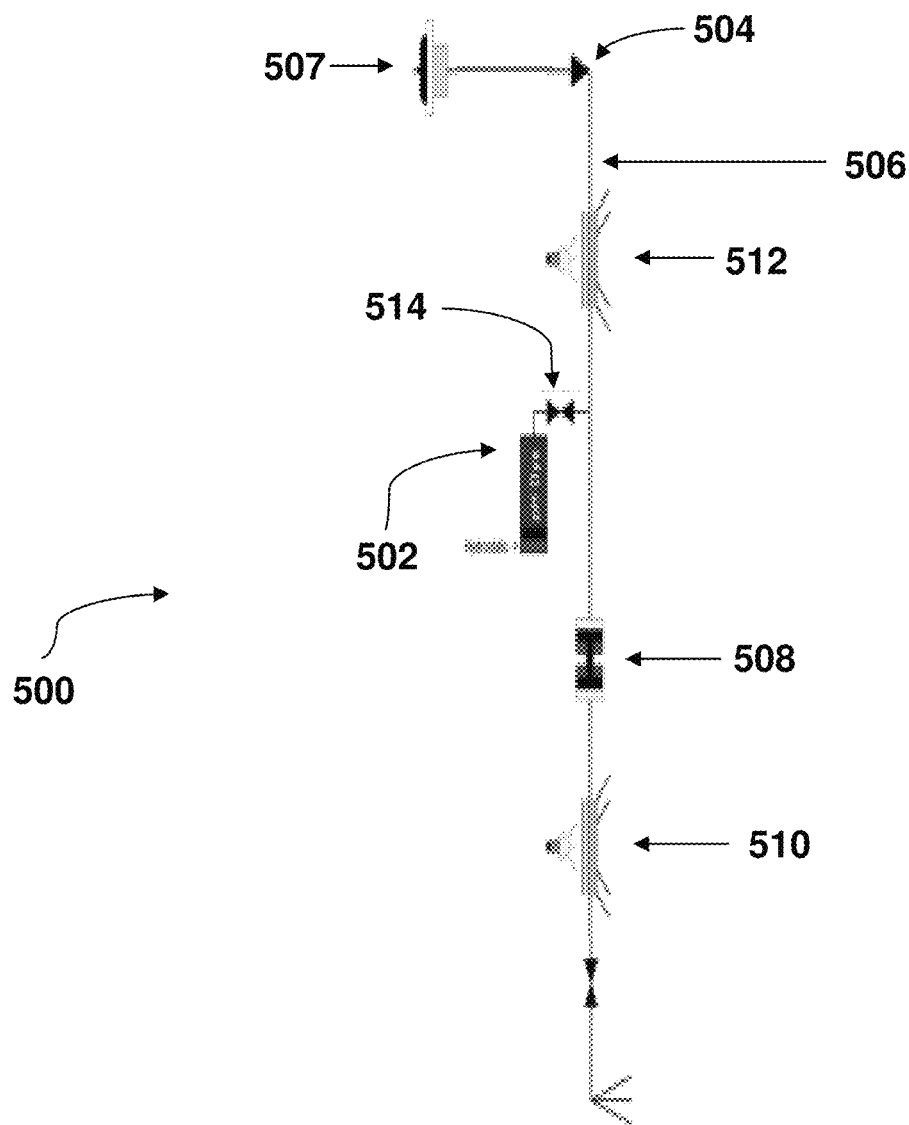
FIG. 5 illustrates a flowline schematic of an embodiment of a tool-string configuration that may be used to measure the volumetric mixing ratio of the fluid sample and the titrant by measuring the optical density of an injected scaling cation insensitive dye.

FIG. 5 illustrates a flowline schematic of an embodiment of a tool-string configuration 500 that may be used to measure the volumetric mixing ratio of the fluid sample and the titrant by measuring the optical density of an injected scaling cation insensitive dye. The titrant solution (counter scaling anions, at least one complexing agent and a scaling cation insensitive dye) may be vacuum-filled into a titrant injection chamber 502 at the surface. The titrant chamber 502 may have a piston exposed to the borehole hydrostatic pressure on the back side. A check valve 504 may be placed in the flowline 506 between the titrant chamber 502 and the sampling probe or packer 507 to prevent the titrant from backflowing into the formation. A pumpout module 508 is positioned between the sampling probe 507 and the optical interrogator 510 to allow for oil/water segregation in mixed-flow systems before optical interrogation. The optical interrogator 510 will see slugs of water and oil, but because the injected titrant may be soluble in the water phase, the optical spectra of the aqueous phase of the mixed solution containing slug may be used to measure the optical density of the scaling cation insensitive dye in such mixed-flow systems, thereby providing a means to determine the volumetric mixing ratio of the fluid sample and the titrant. Optionally, a separate fluid interrogator 512 may be positioned before the titrant injection chamber and be configured to detect percent contamination and/or phase of the sample fluid that is passing through the flowline to optimize the timing of the titrant injection into the sample fluid.

In one or more embodiments, to make a volumetric mixing ratio measurement a titrant solution comprising known concentrations of counter scaling anions, complexing agent, and a scaling cation insensitive dye may be injected from the titrant chamber 502 into a wellbore flowline 506 containing a wellbore and/or formation fluid to create a mixed solution. The amount of titrant solution injected depends on the pressure differential between the titrant chamber 502 (hydrostatic pressure) and the flowline 506 pressure, the pump flow rate of the formation fluid, and the amount of time that the seal valve 514 of the titrant chamber 502 is kept open. Then the mixed solution may be optically interrogated as it flows past the optical interrogator 510 to determine if precipitation of a scaling cation-counter scaling anion has occurred and also to determine the optical density of the scaling cation insensitive dye. In one or more embodiments, the mixed solution may be sampled by the pumpout module 508 and allowed to phase segregate into an aqueous and oil phase, with the titrant remaining in an aqueous phase of the mixed solution, which is then analyzed. To accomplish the measurements, at least one optical interrogator 510 may be configured to obtain measurements at specific wavelengths appropriate for determining precipitation of a scaling cation-counter scaling anion and the optical density of the scaling cation insensitive dye. Additionally, the at least one optical interrogator 510 may possess a reference channel which has zero response to water, the components of the titrant, and the scaling cation-counter scaling anion precipitate.

A scaling cation insensitive dye may be used to determine the mixing ratio in cases where this mixing ratio is unknown.

The intensity of the dye is directly related to the mixing ratio and can thus be used to determine the mixing ratio. A plot of the absorbance due to precipitation versus the complexing agent concentration may be used to determine the barium concentration. For example, the concentration of the complexing agent in the aqueous phase of the mixed solution may be determined by calculating the mixing ratio of the injected solution and the wellbore and/or formation fluid in the wellbore flowline based on the measured optical density of the scaling cation insensitive dye in the aqueous phase of the mixed solution. In one or more embodiments, by knowing the complexing agent concentration in the mixed solution, the scaling cation concentration may be determined by extrapolating, to the endpoint, the plot of absorbance versus volume of wellbore and/or formation fluid from at least two measurements which correlate to mixed solutions with different mixing ratios that also show precipitation of a scaling cation-counter scaling anion compound. In one or more embodiments, one injection of solution into the wellbore flowline may create a mixed solution where variable mixing ratios can be obtained, their optical density measured, and the complexing agent concentration extrapolated as described above to determine the scaling cation concentration. In yet another embodiment, multiple injections into the wellbore flowline may be used to create multiple mixed solutions with variable mixing ratios.

In interpreting the measurement results of the determination of precipitation and optical density of the scaling cation insensitive dye, real time quality control may be performed. Some of the factors that may affect the measurement quality include the amount of titrant injected and its concentration in the mixed solution, baseline noise, and any scattering seen from mud or oil drops. If the added amount of titrant is very high it may saturate the optical interrogators detector and, on the other hand, if the amount added is too low poor signal to noise ratios may result. Further, noise in the baseline measurements may affect the precision of the measurements. If scattering from mud or oil drops is wavelength independent, then a baseline subtraction may account for it, however, wavelength dependent scattering may introduce errors into the measurement. Real time quality control of the measurements and spectra produced is performed to check for these factors and thereby reject measurements in which the quality is compromised.

In one or more embodiments, it may be desirable to remove or clear scaling cation-counter scaling anion precipitate from the fluid conduit after a measurement has been performed. Scaling cation-counter scaling anion precipitate may be removed or cleared by flowing a concentrated complexing agent solution through the area containing the precipitate in order to complex/re-complex and thereby dissolve the scaling cation-counter scaling anion precipitate.

Figure 7:
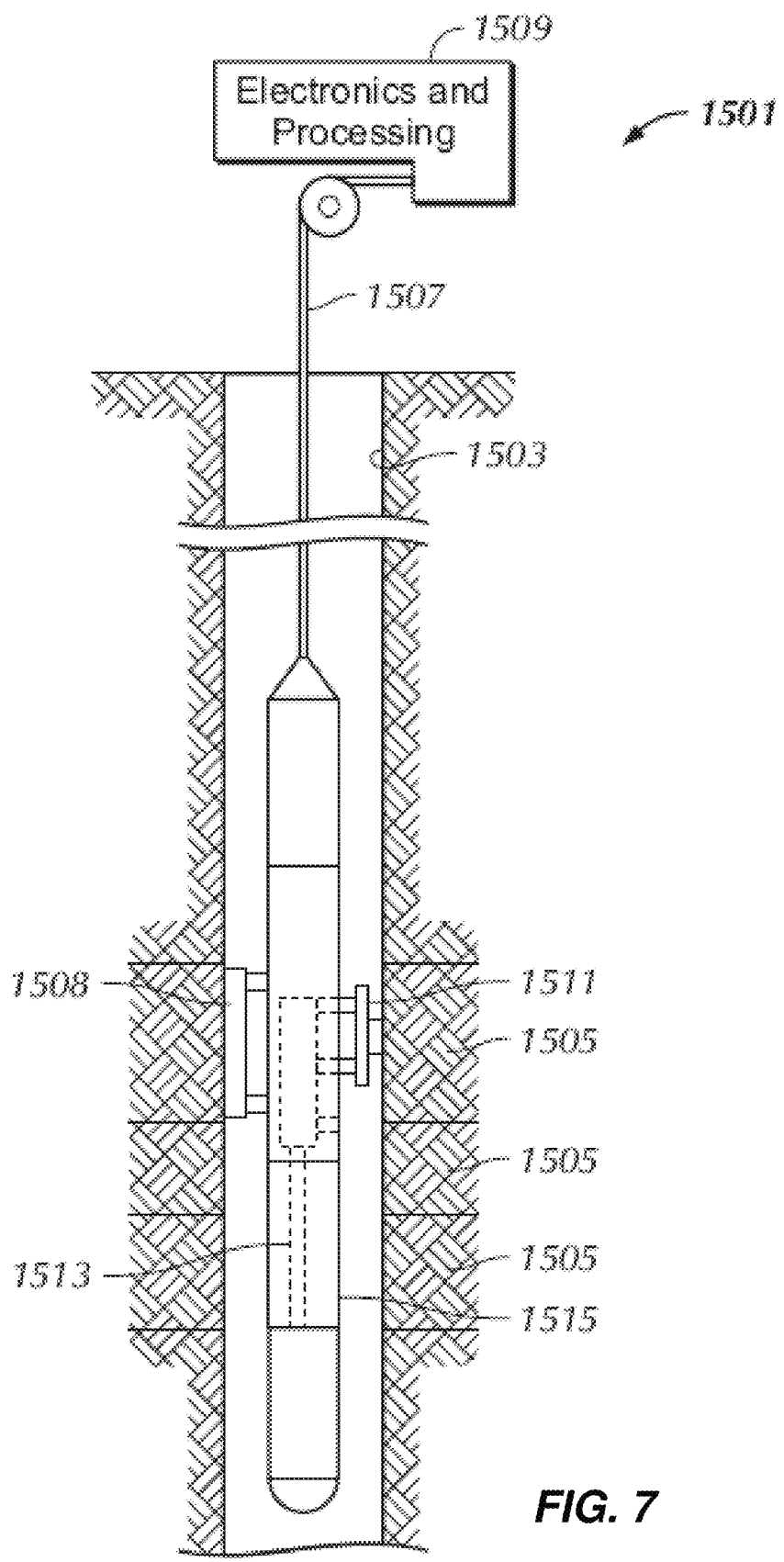
FIG. 7 shows a wireline tool in accordance with one or more embodiments.

In accordance with one or more embodiments, the system designed to perform the measuring recited herein may be deployed as a stand-alone analytical instrument, e.g., as a lab-based analytical instrument or as ruggedized unit for field work, or as part of a downhole logging tool for characterizing downhole fluids, such as a wireline tool or on a drill string. For example, FIG. 7 shows a wireline tool in accordance with one or more embodiments. The wireline tool 1501 is typically lowered into a borehole 1503 that traverses a formation 1505 using a cable 1507. The wireline tool 1501 is lowered down into the borehole 1503 and may make a number of measurements of the adjacent formation at a plurality of sampling locations along the borehole. The data from these measurements is communicated through the cable 1507 to surface equipment 1509, which may include a computer system for storing and processing the data obtained by the wireline tool (e.g., a truck or a cabin on an off-shore platform). The wireline tool 1501 may include a selectively extendable fluid admitting assembly 1511 (e.g., probe). This assembly 1511 extends into the formation 1505 and withdraws formation fluid from the formation (e.g., samples the formation). The fluid flows through the assembly 1511 and into a flow line 1513 within a housing of the tool. In accordance with one or more embodiments, a pump (not shown) may be used to withdraw the formation fluid from the formation 1505 and pass the fluid through the flow line 1513. In accordance with one or more embodiments, the system described herein may be deployed as an additional module 1515 through which the flow line 1513 runs. Accordingly, the system can be used to analyze fluids within the flow line 1513 or other flow lines (not shown) within the wireline tool.

The system described herein is not limited to use with wireline tools or systems. For example, the embodiments described herein can also be used with any suitable means of conveyance, such as coiled tubing or a drill string. Furthermore, various embodiments of the present disclosure may also be applied in logging-while-drilling (LWD) operations, sampling-while-drilling operations, measuring-while-drilling operations, well production operations or any other operation where sampling of fluid is performed.

Embodiments of the methods disclosed herein may be implemented anywhere in the downhole environment, with a tool on a drill string or a wireline. Fluids tested may include formation fluids (such as formation water) injected water, or other wellbore fluids. The fluids to be tested may be pulled into the flowline of the present tool using sample probes and the like used in downhole fluid analyzers. The calculations required to arrive at the concentration of scaling cations from interrogating the fluid sample may be performed downhole by an analyzer component or may be performed at the surface.

In one embodiment, the analyzer component is located near the tool system as part of the analytical control unit. The analytical control unit is in communication with the tool system. In a second embodiment, the analytical control unit is incorporated into the tool system. In yet another embodiment, however, the analytical control unit is located remote from the tool system at an office building or a laboratory to support the tool described above.

The term "analytical control unit" should not be construed to limit the embodiments disclosed herein to any particular device type or system. In one embodiment, the analytical control unit includes a computer system. The computer system may be a laptop computer, a desktop computer, or a mainframe computer. The computer system may include a graphical user interface (GUI) so that a user can interact with the computer system. The computer system may also include a computer processor (e.g., a microprocessor, microcontroller, digital signal processor or general purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. This memory may be used to store, for example, data from analytical instruments.

Some of the methods and processes described above can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Additionally, the analytical control unit may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

EXAMPLES

Figure 4:
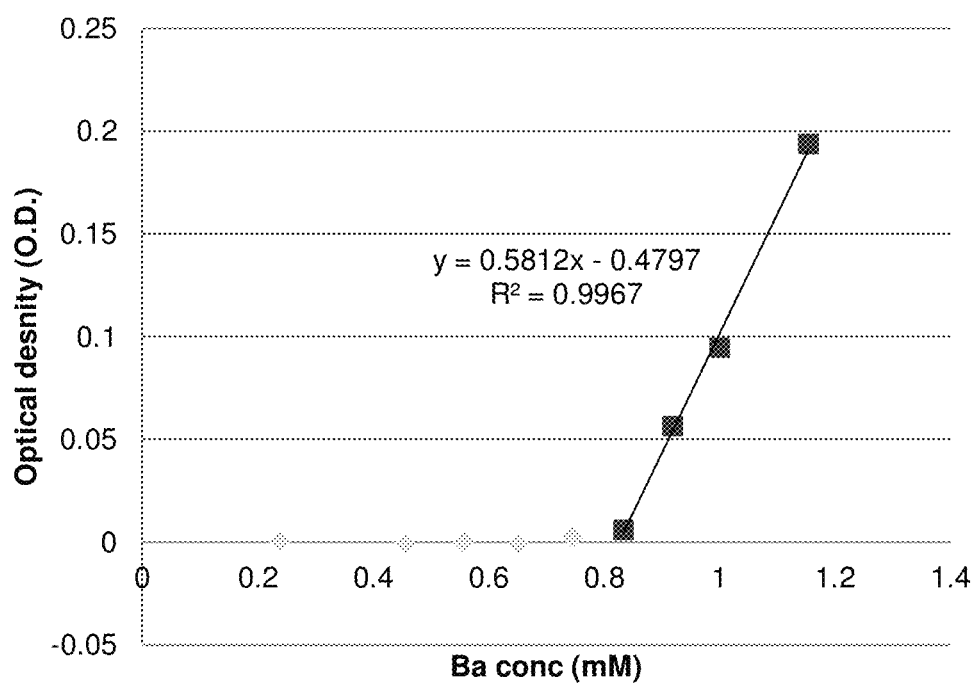
FIG. 4 shows an example absorbance versus $Ba^{2+}$ concentration plot resulting from the addition of $Ba^{2+}$ to a solution comprising EDTA (1 mM) and sulfate (10 mM sulfate) at room temperature.

FIG. 4 shows an example absorbance versus barium concentration plot resulting from the addition of $Ba^{2+}$ ($BaCl_2$) to a solution comprising EDTA (1 mM) and sulfate (10 mM) at room temperature. The optical density is measured at 1070 nm. The expected endpoint is 0.909 mM $Ba^{2+}$. At the point when the EDTA concentration is no longer more than the $Ba^{2+}$ concentration the excess $Ba^{2+}$ cations are able to react with the sulfate and form a precipitate. The precipitate increases the absorbance value and thus provides an onset point of precipitation that may be used to determine the concentration of $Ba^{2+}$ (and any other scaling cations present) as per the equation described above.

Figure 6:
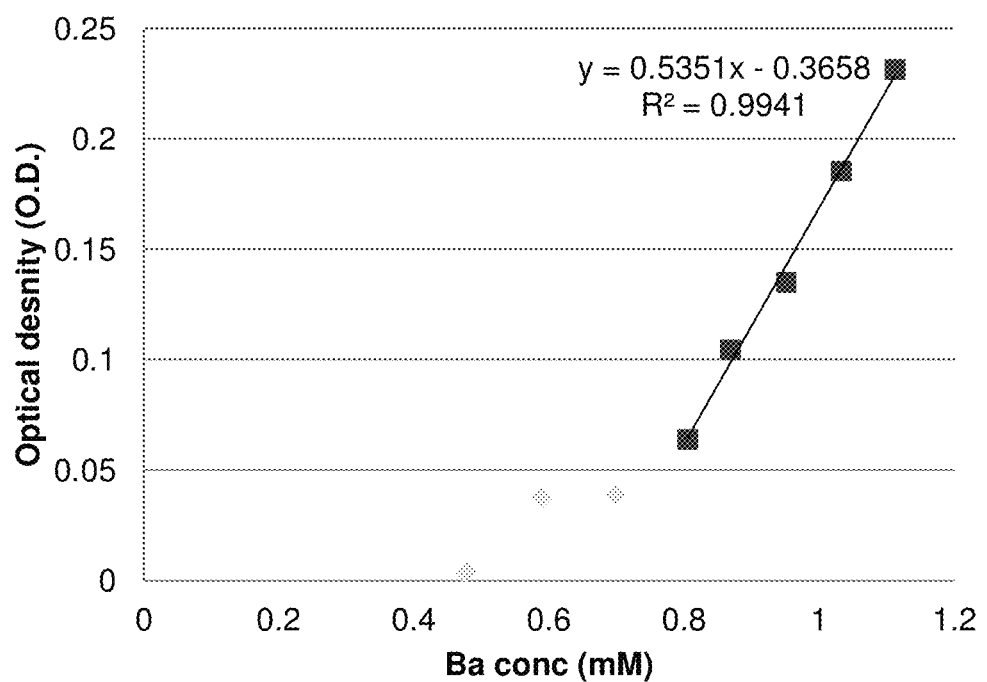
FIG. 6 shows an example absorbance versus barium concentration plot resulting from the addition of $Ba^{2+}$ to a solution comprising EDTA (1 mM) and sulfate (100 mM sulfate) at room temperature.

FIG. 6 shows an example absorbance versus barium concentration plot resulting from the addition of $Ba^{2+}$ to a solution comprising EDTA (1 mM) and sulfate (100 mM sulfate) at room temperature. The optical density is measured at 1070 nm. The expected endpoint is 0.909 mM $Ba^{2+}$. However, in this example the sulfate (counter scaling anion) concentration is much higher than the EDTA concentration (complexing agent) and illustrates that the counter scaling anion, if not kept at most 10 times the concentration of the complexing agent, can compete with the complexing agent for the $Ba^{2+}$ and cause premature precipitation. Premature precipitation leads to the underestimation of the $Ba^{2+}$ concentration, as noted by the increase in absorbance at much lower values than the expected 0.909 mM $Ba^{2+}$.

Embodiments of the present disclosure may provide at least one of the following advantages. Embodiments of the methods described may be implemented in a downhole environment, thereby measuring scaling cation concentration in situ rather than requiring sample transportation to and performing measurements at the surface. However, the present methods may also be performed at the surface without departing from the scope of the present disclosure. Further, embodiments of the methods described herein may allow for the detection of the total amount of scaling cations present within a sample, rather than being limited to a specific scaling cation. The information on scaling cation concentration provided by these methods allows for the timely optimization and refinement of the amount of scale inhibitor needed for a particular operation, thereby saving time and money.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed:

1. A method for determining scaling cation concentration, comprising:
 introducing a first solution comprising a scaling cation;
 incrementally adding a portion of the first solution to a volume of a second solution comprising a counter scaling anion and a complexing agent, wherein the second solution comprises a fixed concentration of the counter scaling anion and the complexing agent, to form a mixed solution;
 adding the first solution to the second solution until a precipitate of the scaling cation and the counter scaling anion forms; and
 determining the scaling cation concentration of the first solution based at least on the amount of said first solution that was added when detecting forming of the precipitate.

2. The method of claim 1, wherein determining the scaling cation concentration comprises relating the amount of the first solution added to form the precipitate in the mixed solution to the concentration of the at least one complexing agent in the second solution.

3. The method of claim 1, wherein determining the scaling cation concentration comprises applying the following equation:

$$X = [Y] * \frac{V_1}{V_2};$$

wherein X is the scaling cation concentration, [Y] is the total complexing agent concentration, $V_1$ is the volume of the second solution, $V_2$ is the volume of the first solution.

4. The method of claim 1, wherein the scaling cations comprise cations of barium, calcium, or strontium, or a combination thereof.

5. The method of claim 1, wherein the complexing agent has a stronger stability constant with the cations of barium, calcium and strontium than non-scale cations.

6. The method of claim 1, wherein the concentration of counter scaling anions in the second solution is less than the concentration of the complexing agent.

7. The method of claim 1, wherein the first solution comprises a formation fluid and/or wellbore fluid.

8. The method of claim 1, wherein the complexing agent comprises at least one iminodiacetic acid group, $N(HCH_2COOH)_2$, or two aminoacetic acid groups, $NHCH_2COOH$.

9. The method of claim 1, wherein the complexing agent comprises phosphonic acid groups.

10. The method of claim 1, wherein the complexing agent comprises at least one crown ether, azacrown ether, cryptand, or substituted analogs thereof.

11. The method of claim 1, wherein the second solution comprises at least two complexing agents.

12. A method for determining scaling cation concentration of a fluid sample within a wellbore, comprising:
- extracting a fluid sample comprising scaling cations from a wellbore and/or formation;
- iteratively adding portions of the extracted fluid sample to a volume of a first solution comprising a counter scaling anion and a complexing agent, wherein the first solution comprises a fixed concentration of the counter scaling anion and the complexing agent, to form a mixed solution;
- optically interrogating the mixed solution to detect precipitation of a scaling cation-counter scaling anion compound; and
- determining the scaling cation concentration based at least on the relative volumes of said extracted fluid sample and said first solution when said precipitation is detected.

13. The method of claim 12, wherein extracting a fluid sample comprises exposing a region of a fluid conduit between open ends of a first reservoir pre-charged with the first solution and a second reservoirs to a high-pressure flow of high-pressure fluids containing scaling cations obtained from a subterranean formation.

14. The method of claim 13, wherein varying a volume of the first reservoir moves the first solution into the fluid conduit.

15. The method of claim 13, wherein the extracted fluid sample is stored in a sample fluid conduit directly exposed to the high-pressure flow of high-pressure fluids containing scaling cations prior to entering the fluid conduit.

16. The method of claim 15, further comprising varying a volume of the second reservoir to draw the fluid sample into the fluid conduit from the sample fluid conduit or to move a solution present in the fluid conduit.

17. The method of claim 12, wherein initially a mixed solution comprising predominantly the first solution is measured and thereafter the measurement is repeated by incrementally increasing the relative amount of the extracted fluid sample in the mixed solution until precipitation of a scaling cation-counter scaling anion compound is detected.

18. The method of claim 12, further comprising agitating the mixed solution with a fluid mixer prior to the optical interrogation.

19. The method of claim 12, wherein the complexing agent has a stronger stability constant with the cations of barium, calcium and strontium than other non-scale cations.

20. The method of claim 12, wherein the first solution comprises at least two complexing agents.

21. A method for determining the scaling cation concentration of a fluid sample within a wellbore, comprising:
- injecting a solution comprising a counter scaling anion, a complexing agent, and a scaling cation insensitive dye into a wellbore flowline containing a wellbore or formation fluid comprising a scaling cation to create a mixed solution;
- determining if precipitation of a scaling cation-counter scaling anion compound has occurred in the mixed solution;
- determining the concentration of the complexing agent in the mixed solution by calculating the mixing ratio of the solution injected and the wellbore or formation fluid based on the optical density of the scaling cation insensitive dye in the mixed solution; and
- determining the scaling cation concentration by extrapolating to the endpoint the plot of absorbance versus the volume of wellbore fluid in the mixed solution of at least two measurements correlated to mixed solutions with different mixing ratios that show precipitation of a scaling cation-counter scaling anion compound.

22. The method of claim 21, further comprising clearing precipitation from the flowline between measurements by the injection of a concentrated complexing agent solution.

23. The method of claim 21, wherein the determining if precipitation of a scaling cation-counter scaling anion has occurred comprises optical interrogation of the mixed solution.

* * * * *